United States Patent [19]

Coe et al.

[11] 4,150,047
[45] Apr. 17, 1979

[54] PROCESS FOR PREPARING HALOGENATED METAL CHELATES

[75] Inventors: Charles G. Coe, Aston; Burton D. Beitchman, Springfield, both of Pa.

[73] Assignee: Air Products and Chemicals, Inc., Allentown, Pa.

[21] Appl. No.: 883,885

[22] Filed: Mar. 6, 1978

[51] Int. Cl.$^2$ .............. C07F 15/06; C07F 15/02; C07F 11/00
[52] U.S. Cl. .................. 260/439 R; 260/429 J; 260/438.1; 260/438.5 R; 260/448 B
[58] Field of Search ......... 260/429 J, 429 R, 438.5 R, 260/439 R, 448 R, 448 B

[56] References Cited

U.S. PATENT DOCUMENTS

| 3,014,939 | 12/1961 | Kluiber | 260/429 J |
| 3,272,853 | 9/1966 | Braun | 260/429 J |
| 3,634,477 | 1/1972 | Chattoraj et al. | 260/429 J |

OTHER PUBLICATIONS

Fernando, Adv. in Inorganic Chem. & Radio Chem., vol. 7, pp. 188–195 (1965).

Primary Examiner—Helen M. S. Sneed
Attorney, Agent, or Firm—Russell L. Brewer; Barry Moyerman

[57] ABSTRACT

This invention relates to an improved process for preparing halogenated metal chelates of beta-dicarbonyl compounds, particularly the tris-brominated acetylacetonates. The process comprises passing elemental halogen through a solution comprising the metal chelate, an inert solvent in which the metal chelate has a solubility of at least 0.5 grams per 100 grams solvent and the halogenated product has a solubility of less than 1 gram per 100 grams solvent and a halogenated Lewis acid at a temperature from about 0°–60° C. thereby forming a halogenated metal chelate precipitate and then recovering the precipitate.

8 Claims, No Drawings

PROCESS FOR PREPARING HALOGENATED METAL CHELATES

BACKGROUND OF THE INVENTION

1. Field of the Invention

This invention relates to a process for preparing halogenated metal chelates of beta-dicarbonyl compounds, and particularly the synthesis of tris-(3-bromo acetylacetonato) metal (III) compounds.

2. Description of the Prior Art

U.S. Pat. No. 3,014,939 discloses as prior art that halogenated analogues of metal chelates of beta-dicarbonyl compounds can be prepared by reacting a halogenated chelate or ligand with a metal salt and that chromium acetylacetonates can be brominated by direct bromination. The patent, however, was granted on the basis that halogenation of the metal chelate of beta-dicarbonyl compounds could be effected by reacting the metal chelate with an N-halogenated cyclic amide such as N-bromosuccinimide.

Other authors have disclosed methods for producing the brominated metal chelates of beta-dicarbonyl compounds by reacting elemental bromine with the metal chelate in the presence of glacial acetic acid. (Presumably, this is the process referred to in U.S. Pat. No. 3,014,939.) The basic problem with this process is that the product decomposes in the glacial acetic acid, and as a result, low yields are experienced.

SUMMARY OF THE INVENTION

This invention relates to an improvement in a process for preparing a halogenated metal chelate product, particularly the brominated metal chelates of beta dicarbonyl compounds by halogenating the metal chelates. The improvement in this process resides in (a) reacting the metal chelate with elemental halogen in an inert solvent in which the metal chelate has a solubility of at least 0.5 grams per 100 grams of solvent and the halogenated product has a solubility of less than 1 gram per 100 grams of solvent and a catalytic quantity of a halogenated Lewis acid to enhance the rate of reaction; (b) establishing and maintaining the reaction temperature at about 0° to 60° and allowing the reaction to proceed until a precipitate of halogenated product forms in the inert solvent and then, (c) recovering the precipitated product from the inert solvent.

Several advantages are associated with the process of this invention, and these advantages include:

- a simple means for continuously removing halogenated metal chelate product from the reaction medium by virtue of its insolubility in the solvent;
- unusually high yields, e.g. greater than 50% and generally above 70% by weight, particularly of the tris-(3-bromoacetylacetonate complex; and
- economy of reaction in that an inexpensive halogenating agent is used to form the halogenated metal chelates.

DESCRIPTION OF THE PREFERRED EMBODIMENTS

The metal chelates which can be halogenated in the practice of this invention, are those metal chelates of betadicarbonyl compounds generally represented by the formula below:

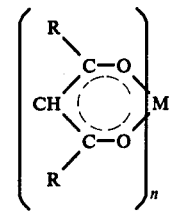

wherein:
- R is a lower alkyl having 1 to 3 carbon atoms, or a phenyl group;
- M represents a polyvalent metal; and
- n is an integer equal in value to the valence of the metal ion M.

The preferred metals used in forming the metal chelates are those having a valence state of +3, and include iron, chromium and cobalt. Other metals suited for practicing the invention include copper, vanadium, nickel, rhodium, aluminum, beryllium, gallium, and iridium.

With respect to the ligand portion, a variety of substituent groups R can be pendant from the acetonato group and include alkyl groups ($C_{1-3}$), aryl groups such as phenyl, naphthyl, aralkyl with $C_{1-3}$ in the alkyl portions such as phenyl ethyl, naphthyl methyl, phenyl propyl; alicyclic such as cyclopentyl, cyclohexyl, and oxygenated derivatives (alkoxy) of hydrocarbons such as methoxymethyl, phenoxyethyl, and so forth. Generally, it is preferred that R is a lower alkyl group having from 1 to 3 carbon atoms (preferably, methyl groups or phenyl groups).

The preferred chelate used in the halogenation process is cobalt acetylacetonate with the cobalt in the +3 valence state. This particular halogenated, and preferably brominated, metal chelate is extremely effective as a catalyst component in curing polyester resins. When coupled with a chemical thickener such as magnesium hydroxide or calcium hydroxide, synergism is observed between the tris-(3-bromo acetylacetonato) cobalt (III) and chemical thickener to provide for enhanced shelf life in unsaturated polyester resin extended with vinyl monomer and to provide for accelerated cure.

Halogenation of the above metal chelates of betadicarbonyl compounds is effected by contacting the metal chelate with elemental halogen. Typically, the halogen, e.g., bromine, iodine or chlorine is passed in liquid or vapor form through a solution comprising the metal chelate and inert solvent. The preferred elemental halogen is bromine as it provides an easy mechanism for producing a preferred brominated metal chelate complex.

Halogenation of the metal chelate is conducted in the presence of a solvent which is inert to the reaction components. By inert it is meant that the solvent will not react with the metal chelate, although it may partially react with the elemental halogen to form a halogenated solvent. With most of the preferred solvents, very little halogenation occurs under the reaction conditions employed. The halogenation reaction described above can be represented by the following equation:

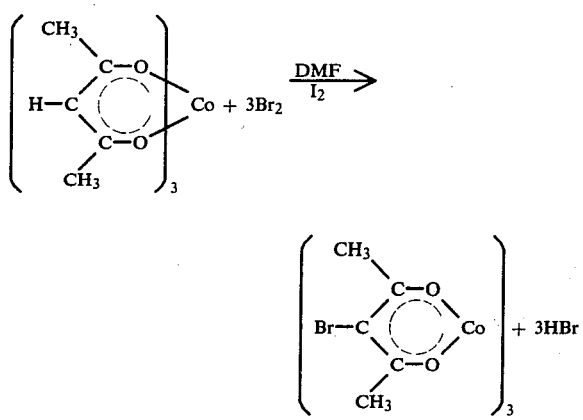

There are essentially three parts to the test that are used in determining whether a solvent is operable in this process and these steps are:
(1) the metal chelate has some solubility in the solvent, at least to the extent that 0.5 grams, preferably 2 grams, will dissolve in 100 grams solvent at a temperature of 20° C.;
(2) the halogenated metal chelate metal product produced is not highly soluble in the solvent generally less than 1 gram per 100 grams of solvent at 20° C.; and
(3) the metal chelate and halogenated metal chelate are unreactive (less than 5% change in 10 hours) with the solvent at a temperature of 60° C. and atmospheric pressure.

By employing a solvent which is inert to the reaction medium and one where the metal chelate is soluble and the product insoluble, it is possible to achieve high yields of product and effect separation of the product from the reaction medium through a simple and efficient means. Examples of solvents which can be used in practicing the invention include N-alkyl amides such as dimethyl acetamide, dimethyl formamide, dimethyl propionamide; N-alkyl pyrrolidones such as N-methyl pyrrolidone. Halogenated paraffins, e.g., carbon tetrachloride, result in decomposition of the product. The preferred solvent for practicing the invention is dimethyl formamide as it is relatively inexpensive, inert under the reaction conditions, and non-toxic thus providing a simplified method of halogenating a metal chelate.

Another of the primary differences in practicing this invention from the halogenation of metal chelates performed heretofore is the inclusion of a halogenated Lewis acid as a promoter for the halogenation reaction. The halogenated Lewis acid should be appropriately selected so that it does not compete with the halogen, i.e., it should be less reactive. For example, if the elemental halogen is chlorine, then the Lewis acid should be a brominated or iodinated Lewis acid, preferably brominated. Where the elemental halogen is bromine, then the Lewis acid should be an iodine or iodine precursor such as $KI_3$. Examples of Lewis acids which are suited for the halogenation reaction includes ferric bromide, $KI_3$, $I_2$, boron trifluoride etherate, aluminum chloride, aluminum and zinc bromide, and the like. In view of the fact that the brominated metal chelate is the preferred product, iodine or an iodine precursor $KI_3$ which liberates free iodine in situ generally is used in practicing the invention.

Typically, the halogenated Lewis acid is employed in a catalytic proportion, e.g., from about 0.01–5 mole percent based on the moles of metal chelate present in the reaction medium. Preferably, the concentration is from about 0.5–1.5%. Concentrations higher than about 3% do not result in significant advantages in terms of enhanced reaction rate or yields. Concentrations less than about 0.01% result in slow reaction times.

Halogenation of the metal chelate generally is accomplished at atmospheric pressure although pressures from atmospheric to 100 psi can be used. Temperatures are generally maintained at from about 0°–60° C., and generally to 50° C. as many of the metal chelates are sensitive to high temperatures and begin decomposing. A temperature of 30° C. is preferred to obtain good, easily controlled reaction rates. This is particularly true of cobaltic acetylacetonate and the tris-bromo acetylacetonate product produced on bromination. Halogenation of the metal chelate can be conducted as rapidly as possible, so long as one can control the heat evolved by the exothermic reaction. In order to permit greater control of the temperature, it is preferable to use a substantial excess of solvent as this provides a mechanism for removing heat and also aids in the mechanical mixing. Generally, the reaction proceeds as rapidly as the halogen material is introduced into the mixture of solvent, metal chelate, and Lewis acid. However, it is possible to enhance reaction completion by adding a stoichiometric excess, e.g. 10–20 mole percent excess of elemental halogen based on the moles metal chelate. Because the product is insoluble in the solvent, it is possible to determine when the reaction is completed by the amount of precipitate formed.

The following examples are provided to illustrate the best and preferred embodiments of the invention and are not intended to restrict the scope thereof. All percentages are expressed as weight percentages and all temperatures are in degrees centigrade.

EXAMPLE 1 — PREPARATION OF TRIS-(3-BROMO ACETYL ACETONATO) COBALT III

A 1,246 gram portion of cobalt (III) acetylacetonate (3.5 moles), 9.1 grams iodine (0.035 moles) and 3,850 cc N,N-dimethylformamide were charged to a 12 liter 3-neck flask equipped with a mechanical stirrer. In a separate vessel, 2,188 grams bromine (13.7 moles) were slowly mixed with 4,200 cc N,N-dimethyl formamide. In an effort to control the temperature, the addition of the bromine to the dimethyl formamide was made slowly and the solution was cooled in an ice bath until the exotherm subsided. The resulting bromine solution was introduced to the 3-neck flask through a 500 cc dropping funnel at a rate of approximately 35 cc per minute, and during addition, a water bath was used to establish and maintain the temperature in the 3-neck flask at about 40° C. After addition of the bromine solution was complete (about 3 hours required), the reaction was stirred for an additional 30 minutes and then the reaction terminated by cooling to ambient temperature (23° C.). Green solids were evident in the reaction mixture and were isolated by filtration. The product then was washed three times with two liters of water and dried in a vacuum oven at 80° C. for about 12 hours. A total of 1,710 grams of product was obtained and the yield was calculated to be 82.4%. Elemental analysis showed

| | C | H | Br | Co |
|---|---|---|---|---|
| Found | 30.12 | 3.13 | 37.2 | 10.07 |
| Theoretical | 30.38 | 3.06 | 40.43 | 9.93 |

These results show good yield and conversion to the tris-(3-bromo acetylacetonato) cobalt (III).

EXAMPLE 2 (PRIOR ART)

A two liter three neck flask equipped with a dropping funnel, mechanical stirrer and thermowell was charged with 30.3g cobaltic acetylacetonate (0.085 mole), 35.6g sodium acetate (0.26 mole) and 750 cc of glacial acetic acid. The dropping funnel was charged with 60g of bromine (0.375 mole) dissolved in 200 cc of glacial acetic. The bromine solution was slowly added to the reaction vessel over an 80 minute period. After two hours at 30° C., the reaction mixture was filtered and the resulting dark green solids washed first with water. The solids were then washed twice with 10% aqueous sodium bicarbonate and 2.5% aqueous sodium bisulfite. Finally, the solids were washed again with water and then dried for about 16 hours at 80° C. under vacuum. The dried crude product melted with decomposition from 161°-65° C. and weighed 18.6g for a yield of 37%.

EXAMPLE 3

The procedure of Example 1 was repeated except that the temperature was permitted to rise to 60° C. during the addition of the bromine-N,N-dimethyl formamide solution. It was observed that the yield was lower, and this was believed to be caused by slight decomposition of the product at these temperatures. Thus, temperatures about 30°-50° C. are preferred in order to achieve higher yield.

EXAMPLE 4

The procedure of Example 1 was repeated except that the catalyst employed was 1 mole % ferric bromide instead of the iodine and the temperature was permitted to rise to 60° C. The reaction produced a 69% yield of pure product and again the lower yield is believed to be a result of the higher temperature.

EXAMPLE 5

The procedure of Example 1 was repeated except that a 50% excess of bromine was employed. This reaction produced no significant improvement in the yield (81 versus 82%) of tris 3-bromoacetylacetonato cobalt (III).

EXAMPLE 6

The procedure described in Example 1 was repeated except that the Lewis acid catalyst was doubled to 2 mole % iodine. Doubling the catalyst concentration resulted in similar yield of product (81 versus 82%). Higher yields of the tris 3-bromoacetylacetonato cobalt (III) can be obtained by recycling the spent DMF reaction solvent from a previous run. By adding the spent DMF solvent to the bromine stream and accounting for any unreacted cobaltic acetylacetonate present, the yield of the brominated product was increased to 98.7%.

What is claimed is:

1. A process for halogenating a metal chelate of the formula:

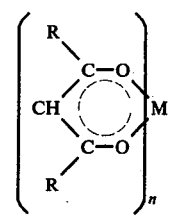

wherein:
R is a lower alkyl having 1 to 3 carbon atoms, alkoxy or phenyl;
M is a polyvalent metal ion selected from the group consisting of cobalt, iron and chromium; and
n is an integer equal to the valence of the polyvalent metal,
to form a halogenated product represented by the following structure:

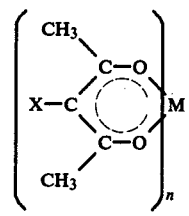

where X = Cl, Br, or I which comprises the steps:
(a) contacting elemental halogen with a solution comprising said metal chelate, an inert solvent in which the solubility of said metal chelate is at least 0.5 grams per 100 grams and the solubility of the halogenated product is less than 1 gram per 100 grams, said solvent selected from the group consisting of N-alkyl amides, N-alkyl pyrrolidone, and N,N'-dialkyl amides wherein the alkyl groups have from 1 to 3 carbon atoms in the respective alkyl portion and a catalytic quantity of a halogenated Lewis acid;
(b) establishing and maintaining a temperature of from about 0°-60° C. for a time sufficient to form a halogenated precipitate; and
(c) recovering said halogenated precipitate as product.

2. The process of claim 1 wherein said Lewis acid is present in a proportion of from about 0.01 to 5 mole percent based on the moles metal chelate.

3. The process of claim 2 wherein halogenated Lewis acid is selected from the group consisting of iodine and iodine precursors.

4. The process of claim 3 wherein R in said metal chelate is methyl.

5. The process of claim 4 wherein said polyvalent metal is cobalt and n is three.

6. The process of claim 5 wherein the temperature is maintained from about 30°-50° C.

7. The process of claim 5 wherein said solvent is N,N-dimethyl formamide.

8. The process of claim 7 wherein said halogenated Lewis acid is iodine and is present in a proportion of from 0.5-1.5% based on the moles of metal chelate.

* * * * *